（12） United States Patent
Hunt et al.

(10) Patent No.: US 10,307,548 B1
(45) Date of Patent: Jun. 4, 2019

(54) TRACKING SYSTEM AND METHOD FOR MEDICAL DEVICES

(71) Applicants: Timothy Brandon Hunt, Ft. Lauderdale, FL (US); Jonathan J. Vitello, Ft. Lauderdale, FL (US)

(72) Inventors: Timothy Brandon Hunt, Ft. Lauderdale, FL (US); Jonathan J. Vitello, Ft. Lauderdale, FL (US)

( * ) Notice: Subject to any disclaimer, the term of this patent is extended or adjusted under 35 U.S.C. 154(b) by 0 days.

(21) Appl. No.: 15/842,446

(22) Filed: Dec. 14, 2017

Related U.S. Application Data

(60) Provisional application No. 62/434,259, filed on Dec. 14, 2016.

(51) Int. Cl.
*A61M 5/50* (2006.01)

(52) U.S. Cl.
CPC ..... *A61M 5/5086* (2013.01); *A61M 2205/583* (2013.01); *A61M 2205/6009* (2013.01); *A61M 2205/6072* (2013.01)

(58) Field of Classification Search
CPC .... A61M 2205/583; A61M 2205/6072; A61M 2205/6009
See application file for complete search history.

(56) References Cited

U.S. PATENT DOCUMENTS

| | | |
|---|---|---|
| 732,662 A | 6/1903 | Smith |
| 1,678,991 A | 7/1928 | Marschalek |
| 1,970,631 A | 8/1934 | Sherman |
| 2,477,598 A | 8/1949 | Hain |
| 2,739,590 A | 3/1956 | Yochem |
| 2,823,674 A | 2/1958 | Yochem |
| 2,834,346 A | 5/1958 | Adams |
| 2,875,761 A | 3/1959 | Helmer et al. |
| 2,888,015 A | 5/1959 | Hunt |
| 2,952,255 A | 9/1960 | Hein, Jr. |
| 3,122,280 A | 2/1964 | Goda |
| 3,245,567 A | 4/1966 | Knight |
| 3,323,798 A | 6/1967 | Miller |
| 3,364,890 A | 1/1968 | Andersen |
| 3,598,120 A | 8/1971 | Mass |
| 3,610,241 A | 10/1971 | LeMarie |

(Continued)

FOREIGN PATENT DOCUMENTS

| EP | 0148116 A | 7/1985 |
|---|---|---|
| WO | WO 2017086607 | 5/2015 |

*Primary Examiner* — Fekadeselassie Girma
(74) *Attorney, Agent, or Firm* — Malloy & Malloy, P.L.

(57) ABSTRACT

A tracking system for medical devices which may include a closure and a container and a method for implementation the tracking system. Packaging removably retains the closure therein and a label is connected to the closure in an at least initially reduced orientation within the packaging. The packaging is structured for receipt of at least a portion of the container to establish an attached relation to the closure, whereupon the attached closure and container are concurrently removed from the packaging. The label is disposed in an expanded orientation and connected to both the closure and the container and includes a coded identifier having at least first and second coded segments. The coded identifier, including the first and second coded segments, include coded indicia may be machine readable and structured to define an identifying, matching relation of the closure and the container.

19 Claims, 6 Drawing Sheets

(56) References Cited

U.S. PATENT DOCUMENTS

| | | | |
|---|---|---|---|
| 3,700,215 A | 10/1972 | Hardman et al. | |
| 3,706,307 A | 12/1972 | Hasson | |
| 3,712,749 A | 1/1973 | Roberts | |
| 3,747,751 A | 7/1973 | Miller et al. | |
| 3,872,867 A | 3/1975 | Killinger | |
| 3,905,375 A | 9/1975 | Toyama | |
| 3,937,211 A | 2/1976 | Merten | |
| 4,043,334 A | 8/1977 | Brown et al. | |
| 4,046,145 A | 9/1977 | Choksi et al. | |
| 4,216,585 A | 8/1980 | Hatter | |
| 4,216,872 A | 8/1980 | Bean | |
| 4,244,366 A | 1/1981 | Raines | |
| 4,252,122 A | 2/1981 | Halvorsen | |
| 4,286,591 A | 9/1981 | Raines | |
| 4,313,539 A | 2/1982 | Raines | |
| 4,420,085 A | 12/1983 | Wilson et al. | |
| 4,430,077 A | 2/1984 | Mittleman et al. | |
| 4,457,445 A | 7/1984 | Hanks et al. | |
| 4,521,237 A | 6/1985 | Logothetis | |
| 4,530,697 A | 7/1985 | Kuhlemann et al. | |
| 4,571,242 A | 2/1986 | Klein et al. | |
| 4,589,171 A | 5/1986 | McGill | |
| 4,667,837 A | 5/1987 | Vitello et al. | |
| 4,693,707 A | 9/1987 | Dye | |
| 4,726,483 A | 2/1988 | Drozd | |
| 4,743,229 A | 5/1988 | Chu | |
| 4,743,231 A | 5/1988 | Kay et al. | |
| 4,760,847 A | 8/1988 | Vaillancourt | |
| 4,832,695 A | 5/1989 | Rosenberg et al. | |
| 4,834,706 A | 5/1989 | Beck et al. | |
| 4,842,592 A | 6/1989 | Caggiani et al. | |
| 4,844,906 A | 7/1989 | Hermelin et al. | |
| 4,906,231 A | 3/1990 | Young | |
| 4,919,285 A | 4/1990 | Roof et al. | |
| 5,009,323 A | 4/1991 | Montgomery et al. | |
| 5,049,129 A | 9/1991 | Zdeb et al. | |
| 5,057,093 A | 10/1991 | Clegg et al. | |
| 5,135,496 A | 8/1992 | Vetter et al. | |
| 5,165,560 A | 11/1992 | Ennis, III et al. | |
| 5,230,429 A | 7/1993 | Etheredge, III | |
| 5,267,983 A | 12/1993 | Oilschlager et al. | |
| 5,292,308 A | 3/1994 | Ryan | |
| 5,295,599 A | 3/1994 | Smith | |
| 5,328,466 A | 7/1994 | Denmark | |
| 5,328,474 A | 7/1994 | Raines | |
| 5,356,380 A | 10/1994 | Hoekwater et al. | |
| 5,380,295 A | 1/1995 | Vacca | |
| 5,405,339 A | 4/1995 | Kohnen et al. | |
| 5,458,580 A | 10/1995 | Hajishoreh | |
| 5,468,224 A | 11/1995 | Souryal | |
| 5,531,695 A | 7/1996 | Swisher | |
| 5,540,666 A | 7/1996 | Barta et al. | |
| 5,549,571 A | 8/1996 | Sak | |
| 5,558,648 A | 9/1996 | Shields | |
| 5,584,817 A | 12/1996 | van den Haak | |
| 5,588,239 A * | 12/1996 | Anderson | G09F 3/0289 283/81 |
| 5,624,402 A | 4/1997 | Imbert | |
| 5,674,209 A | 10/1997 | Yarger | |
| 5,700,247 A | 12/1997 | Grimard et al. | |
| 5,702,374 A | 12/1997 | Johnson | |
| 5,776,124 A | 7/1998 | Wald | |
| 5,785,691 A | 7/1998 | Vetter et al. | |
| 5,797,885 A | 8/1998 | Rubin | |
| 5,807,343 A | 9/1998 | Tucker et al. | |
| 5,883,806 A | 3/1999 | Meador et al. | |
| 5,884,457 A | 3/1999 | Ortiz et al. | |
| 5,902,269 A | 5/1999 | Jentzen | |
| 5,951,522 A | 9/1999 | Rosato et al. | |
| 5,951,525 A | 9/1999 | Thorne et al. | |
| 5,954,657 A | 9/1999 | Rados | |
| 5,957,166 A | 9/1999 | Safabash | |
| 5,989,227 A | 11/1999 | Vetter et al. | |
| 6,000,548 A | 12/1999 | Tsals | |
| 6,021,824 A | 2/2000 | Larsen et al. | |
| 6,027,482 A | 2/2000 | Imbert | |
| 6,068,614 A | 5/2000 | Kimber et al. | |
| 6,126,640 A | 10/2000 | Tucker et al. | |
| 6,190,364 B1 | 2/2001 | Imbert | |
| 6,193,688 B1 | 2/2001 | Balestracci et al. | |
| 6,196,593 B1 * | 3/2001 | Petrick | G09F 3/02 283/101 |
| 6,196,998 B1 | 3/2001 | Jansen et al. | |
| 6,235,376 B1 * | 5/2001 | Miyazaki | G09F 3/02 428/195.1 |
| 6,280,418 B1 | 8/2001 | Reinhard et al. | |
| 6,287,671 B1 * | 9/2001 | Bright | B65C 3/16 156/84 |
| 6,322,543 B1 | 11/2001 | Singh et al. | |
| 6,338,200 B1 | 1/2002 | Baxa et al. | |
| 6,375,640 B1 | 4/2002 | Teraoka | |
| 6,394,983 B1 | 5/2002 | Mayoral et al. | |
| 6,485,460 B2 | 11/2002 | Eakins et al. | |
| 6,500,155 B2 | 12/2002 | Sasso | |
| 6,520,935 B1 | 2/2003 | Jansen et al. | |
| 6,540,697 B2 | 4/2003 | Chen | |
| 6,565,529 B1 | 5/2003 | Kimber et al. | |
| 6,581,792 B1 | 6/2003 | Limanjaya | |
| 6,585,691 B1 * | 7/2003 | Vitello | A61M 5/3134 215/230 |
| 6,592,251 B2 | 7/2003 | Edwards et al. | |
| 6,682,798 B1 * | 1/2004 | Kiraly | B42D 15/006 281/5 |
| 6,726,652 B2 | 4/2004 | Eakins et al. | |
| 6,726,672 B1 | 4/2004 | Hanley et al. | |
| 6,755,220 B2 | 6/2004 | Castellano et al. | |
| 6,764,469 B2 | 7/2004 | Broselow | |
| 6,821,268 B2 | 11/2004 | Balestracci | |
| 6,921,383 B2 | 7/2005 | Vitello | |
| 6,942,643 B2 | 9/2005 | Eakins et al. | |
| 7,055,273 B2 * | 6/2006 | Roshkoff | G09F 3/10 40/594 |
| 7,141,286 B1 | 11/2006 | Kessler et al. | |
| 7,182,256 B2 | 2/2007 | Andreasson et al. | |
| 7,240,926 B2 | 7/2007 | Dalle et al. | |
| 7,374,555 B2 | 5/2008 | Heinz et al. | |
| 7,404,500 B2 | 7/2008 | Marteau et al. | |
| 7,410,803 B2 | 8/2008 | Nollert et al. | |
| 7,425,208 B1 | 9/2008 | Vitello | |
| 7,437,972 B2 | 10/2008 | Yeager | |
| 7,482,166 B2 | 1/2009 | Nollert et al. | |
| 7,588,563 B2 | 9/2009 | Guala | |
| 7,594,681 B2 | 9/2009 | DeCarlo | |
| 7,632,244 B2 | 12/2009 | Buehler et al. | |
| 7,641,636 B2 | 1/2010 | Moesli et al. | |
| 7,735,664 B1 | 6/2010 | Peters et al. | |
| 7,748,892 B2 | 7/2010 | McCoy | |
| 7,762,988 B1 | 7/2010 | Vitello | |
| 7,766,919 B2 | 8/2010 | Delmotte | |
| 7,802,313 B2 | 9/2010 | Czajka | |
| 7,918,830 B2 | 4/2011 | Langan et al. | |
| 8,079,518 B2 | 12/2011 | Turner et al. | |
| 8,091,727 B2 | 1/2012 | Domkowski | |
| 8,137,324 B2 | 3/2012 | Bobst | |
| 8,140,349 B2 | 3/2012 | Hanson et al. | |
| 8,257,286 B2 | 9/2012 | Meyer et al. | |
| 8,328,082 B1 | 12/2012 | Bochenko et al. | |
| 8,348,895 B1 | 1/2013 | Vitello | |
| 8,353,869 B2 | 1/2013 | Ranalletta et al. | |
| 8,443,999 B1 | 5/2013 | Reinders | |
| D684,057 S | 6/2013 | Kwon | |
| 8,512,277 B2 | 8/2013 | Del Vecchio | |
| 8,556,074 B2 | 10/2013 | Turner et al. | |
| 8,579,116 B2 | 11/2013 | Pether et al. | |
| 8,591,462 B1 | 11/2013 | Vitello | |
| 8,597,255 B2 | 12/2013 | Emmott et al. | |
| 8,597,271 B2 | 12/2013 | Langan et al. | |
| 8,616,413 B2 | 12/2013 | Koyama | |
| D701,304 S | 3/2014 | Lair et al. | |
| 8,672,902 B2 | 3/2014 | Ruan et al. | |
| 8,702,674 B2 | 4/2014 | Bochenko | |
| 8,777,930 B2 | 7/2014 | Swisher et al. | |
| 8,852,561 B2 | 10/2014 | Wagner et al. | |
| 8,864,021 B1 | 10/2014 | Vitello | |

(56) References Cited

U.S. PATENT DOCUMENTS

| | | |
|---|---|---|
| 8,864,707 B1 | 10/2014 | Vitello |
| 8,864,708 B1 | 10/2014 | Vitello |
| 8,945,082 B2 | 2/2015 | Geiger et al. |
| 9,101,534 B2 | 8/2015 | Bochenko |
| 9,199,042 B2 | 12/2015 | Farrar et al. |
| 9,199,749 B1 | 12/2015 | Vitello |
| 9,220,486 B2 | 12/2015 | Schweiss et al. |
| 9,220,577 B2 | 12/2015 | Jessop et al. |
| 9,272,099 B2 | 3/2016 | Limaye et al. |
| 9,311,592 B1 | 4/2016 | Vitello et al. |
| D756,777 S | 5/2016 | Berge et al. |
| 9,336,669 B2 | 5/2016 | Bowden et al. |
| D759,486 S | 6/2016 | Ingram et al. |
| 9,402,967 B1 | 8/2016 | Vitello |
| 9,427,715 B2 | 8/2016 | Palazzolo et al. |
| 9,433,768 B2 | 9/2016 | Tekeste et al. |
| 9,463,310 B1 | 10/2016 | Vitello |
| D773,043 S | 11/2016 | Insgram et al. |
| D789,529 S | 6/2017 | Davis et al. |
| 9,687,249 B2 | 6/2017 | Hanlon et al. |
| D797,928 S | 9/2017 | Davis et al. |
| D797,929 S | 9/2017 | Davis et al. |
| 9,855,191 B1 | 1/2018 | Vitello et al. |
| D815,945 S | 4/2018 | Fischer |
| D825,746 S | 8/2018 | Davis et al. |
| 2001/0034506 A1* | 10/2001 | Hirschman ........ A61M 5/14546 604/207 |
| 2001/0056258 A1* | 12/2001 | Evans ................ G06F 19/3468 604/131 |
| 2002/0023409 A1 | 2/2002 | Py |
| 2002/0097396 A1* | 7/2002 | Schafer ................ B07C 5/10 356/240.1 |
| 2002/0099334 A1* | 7/2002 | Hanson ............... A61M 5/1456 604/189 |
| 2002/0101656 A1* | 8/2002 | Blumenthal ......... G02B 25/002 359/440 |
| 2002/0133119 A1 | 9/2002 | Eakins et al. |
| 2003/0146617 A1* | 8/2003 | Franko, Sr. ....... G06K 19/07758 283/81 |
| 2003/0183547 A1 | 10/2003 | Heyman |
| 2004/0064095 A1 | 4/2004 | Vitello |
| 2004/0116858 A1 | 6/2004 | Heinz et al. |
| 2004/0186437 A1 | 9/2004 | Frenette et al. |
| 2004/0225258 A1 | 11/2004 | Balestracci |
| 2005/0146081 A1 | 7/2005 | MacLean et al. |
| 2005/0148941 A1 | 7/2005 | Farrar et al. |
| 2005/0209555 A1 | 9/2005 | Middleton et al. |
| 2006/0084925 A1 | 4/2006 | Ramsahoye |
| 2006/0089601 A1 | 4/2006 | Dionigi |
| 2006/0173415 A1 | 8/2006 | Cummins |
| 2006/0189933 A1* | 8/2006 | Alheidt ................ A61M 5/326 604/110 |
| 2007/0060898 A1 | 3/2007 | Shaughnessy et al. |
| 2007/0106234 A1 | 5/2007 | Klein |
| 2007/0142786 A1 | 6/2007 | Lampropoulos et al. |
| 2007/0191690 A1* | 8/2007 | Hasse ................ A61M 5/14546 600/300 |
| 2007/0219503 A1* | 9/2007 | Loop ................ A61M 5/31511 604/187 |
| 2007/0257111 A1* | 11/2007 | Ortenzi ............. A61M 5/14546 235/385 |
| 2008/0068178 A1 | 3/2008 | Meyer |
| 2008/0097310 A1 | 4/2008 | Buehler et al. |
| 2008/0106388 A1* | 5/2008 | Knight ............. A61M 5/31511 340/10.42 |
| 2008/0243088 A1* | 10/2008 | Evans ............... A61M 5/31525 604/246 |
| 2008/0306443 A1* | 12/2008 | Neer ..................... A61M 5/007 604/121 |
| 2009/0099552 A1 | 4/2009 | Levy et al. |
| 2009/0149815 A1 | 6/2009 | Kiel et al. |
| 2009/0326481 A1 | 12/2009 | Swisher et al. |
| 2010/0084403 A1 | 4/2010 | Popish et al. |
| 2010/0126894 A1 | 5/2010 | Koukol et al. |
| 2010/0179822 A1* | 7/2010 | Reppas .................. G06Q 10/08 705/2 |
| 2010/0228226 A1* | 9/2010 | Nielsen ................ A61M 5/158 604/506 |
| 2010/0252564 A1 | 10/2010 | Martinez et al. |
| 2010/0283238 A1 | 11/2010 | Deighan et al. |
| 2011/0044850 A1 | 2/2011 | Solomon et al. |
| 2011/0046550 A1 | 2/2011 | Schiller et al. |
| 2011/0046603 A1 | 2/2011 | Felsovalyi et al. |
| 2012/0064515 A2* | 3/2012 | Knapp ............... A61B 10/0096 435/6.1 |
| 2012/0096957 A1 | 4/2012 | Ochman |
| 2012/0110950 A1 | 5/2012 | Schraudolph |
| 2013/0018356 A1 | 1/2013 | Prince et al. |
| 2013/0088354 A1* | 4/2013 | Thomas ................ A61B 90/96 340/572.1 |
| 2013/0237949 A1* | 9/2013 | Miller .................. A61M 5/162 604/500 |
| 2014/0000781 A1* | 1/2014 | Franko, Jr. ........... B65C 9/2217 156/60 |
| 2014/0034536 A1* | 2/2014 | Reinhardt ........... A61F 13/0008 206/440 |
| 2014/0069829 A1* | 3/2014 | Evans .................... A24F 23/02 206/265 |
| 2014/0135738 A1 | 5/2014 | Panian |
| 2014/0155868 A1 | 6/2014 | Nelson et al. |
| 2014/0257843 A1* | 9/2014 | Adler .................... G09F 3/0289 705/2 |
| 2014/0326727 A1* | 11/2014 | Jouin ................. B65D 77/2032 220/270 |
| 2014/0353196 A1* | 12/2014 | Key ....................... G09F 3/0288 206/459.1 |
| 2015/0191633 A1* | 7/2015 | De Boer ................ C09J 151/06 250/492.1 |
| 2015/0305982 A1* | 10/2015 | Bochenko ............. A61J 1/2096 604/404 |
| 2015/0310771 A1* | 10/2015 | Atkinson .............. G09F 3/0297 40/5 |
| 2016/0067422 A1 | 3/2016 | Davis et al. |
| 2016/0090456 A1* | 3/2016 | Ishimaru ................ C08J 5/18 428/131 |
| 2016/0144119 A1* | 5/2016 | Limaye ................ B65B 63/005 604/506 |
| 2016/0158110 A1* | 6/2016 | Swisher ............... A61J 15/0026 604/535 |
| 2016/0158449 A1 | 6/2016 | Limaye et al. |
| 2016/0176550 A1 | 6/2016 | Vitello et al. |
| 2016/0328586 A1 | 11/2016 | Bowden et al. |
| 2016/0361235 A1 | 12/2016 | Swisher |
| 2016/0367439 A1 | 12/2016 | Davis et al. |
| 2017/0014310 A1 | 1/2017 | Hyun et al. |
| 2017/0124289 A1* | 5/2017 | Hasan ................. G06F 19/3481 |
| 2017/0173321 A1* | 6/2017 | Davis .................... A61M 39/10 |
| 2017/0203086 A1* | 7/2017 | Davis .................... A61J 15/0076 |
| 2017/0319438 A1* | 11/2017 | Davis .................... A61M 39/1011 |
| 2018/0001540 A1* | 1/2018 | Byun .................... B29C 49/2408 |
| 2018/0089593 A1* | 3/2018 | Patel .................... G06F 8/00 |

* cited by examiner

TRACKING SYSTEM AND METHOD FOR MEDICAL DEVICES

CLAIM OF PRIORITY

This Non-Provisional patent application claims priority to a currently U.S. provisional patent application having Ser. No. 62/434,259 and a filing date of Dec. 14, 2016, which is incorporated herein by reference in its entirety.

BACKGROUND OF THE INVENTION

Field of the Invention

The present invention is directed to a tracking system and its method of implementation incorporating a "coded identifier" disposed on a label, which may be machine-readable and which is indicative of attempted access to a medical container and an attached original closure, along a distribution route. The coded identifier defines an identifying, matching relation of the closure and container, as originally attached to one another, and may be determinative of an unauthorized substitution of either the original closure or container, which indicates tampering along the distribution route.

Description of the Related Art

It is common practice in hospitals and other medical facilities to use pre-loaded or filled syringes, typically prepared by a pharmacist, or other authorized personnel within the medical facility. Such pre-loaded or pre-filled syringes are prepared at an appropriate location convenient for subsequent dispensing to one or more nursing stations or other distribution points, and eventually to patients for administration. The pharmacy or other location where syringes are filled can and often will be located in a remote part of the medical facility, at least relative to the patient care area where administration occurs. In some cases, the loading of syringes occurs in another building or facility entirely, often referred to as "third party pharmacies." This may even be a growing trend among hospitals to limit certain costs. Regardless, a syringe filling station at a large medical facility may resemble a factory, from which drug loaded syringes are delivered to a large number of nurse's stations in multiple hospital or medical buildings. Because many nurse's stations or other dispensing locations are typically located remote from a syringe filling station, a loaded syringe is quite often given to more than one person for delivery to a distribution station and subsequent dosing of the patient.

From the foregoing, it may be understood that during the course of loading a syringe with a drug, and also afterwards, when a loaded syringe is delivered to a distribution station, or even subsequently to a patient, the syringe can easily be handled by a plurality of individuals. This, in turn, increases the chance for the syringe to become contaminated, by exposure to bacteria, germs, etc., which could possibly then be introduced to the patient. Consequently, the concern for and the high level of importance associated with maintaining both the sterility and integrity of a syringe and its contents is well understood.

Also, and especially in the case of a very expensive drug or an addictive drug, such as but not limited to morphine, there is some danger that a pre-loaded syringe will be tampered with by a person seeking to improperly gain access to the drug. A resulting danger also exists in that if an unauthorized access was accomplished, an inappropriate substitute such as saline, might be substituted for the original medicine or drug contained within the prefilled syringe. By way of example only, if saline solution were substituted for a dose of morphine, this could have extremely serious consequences. Thus, the growing use of pre-loaded syringes enhances the need to determine if authorized or unauthorized access has been attempted and/or if the pre-loaded syringe and its contents have been exposed to contamination or otherwise compromised. Accordingly, the benefits of using a pre-filled syringe, and of being able to readily determine whether or not it has been tampered with, are abundantly clear.

Despite attempts in the past to prevent unauthorized access to syringe(s) pre-loaded with a drug or medication, it is understood that some problems continue to exist in this field of art. Such problems include the ability to manufacture syringes, and/or accessories therefor, in an inexpensive and yet effective manner. Other problems exist relative to the number of people that might handle pre-filled syringes, which in turn, poses a challenge to maintaining the sterility of the syringes and/or accessories, whether during storage at the manufacturing facility, during the transport thereof from such a facility to a hospital or other medical facility, and then to a nursing station and ultimately, to a patient care area.

Accordingly, there is a need in the relevant field of art for an improved closure, which may include tamper evident capabilities and which may be used for a variety of medical containers including, but not limited to pre-loaded syringes. The development of an improved syringe closure should overcome problems and or disadvantages of the type set forth above or otherwise known to still exist in this field of art.

In addition, as technology evolves with drug compounding and admixing, the need exists for not only a tamper evident closure such as outlined above, as well as one which provides a clear visual indication of mis-use, but also an improved technology for ensuring the originality of various medical components, such as both a container for a drug and a closure therefor, which should help to ensure the contained drug's purity or purity of other contents within the original container. Therefore, it would highly desirable if a system and method of implementation were developed which included a machine-readable identifier which facilitates the tracking and matched identity of a closure and attach container along a distribution route from point of origin to point of use. Any such identifier would preferably be physically associated with the closure and the container in a manner which identifies and defines a "matching relation" between the closure and the container along the distribution route. As such, any such tracking system developed should quickly, efficiently and accurately establish the original identification of the closure and the container, as being originally assembled with one another, and wherein the closure of the container would maintain an attached relation throughout the entire distribution route.

Further, any such tracking system and method of implementation would preferably also facilitate both the visual indication of attempted access or tampering, as well as the ability to mechanically/electronically read the identifier along each of a plurality of stations along a particular route, including those associated with the assembly, filling, distribution, and administration.

SUMMARY OF THE INVENTION

The present invention is intended to present a solution to these and other needs which remain in the relevant field of art, and as such, is directed to a tracking system for medical devices and a method for implementing the tracking system.

Accordingly, the tracking system includes a closure and a packaging for the closure, wherein the closure is initially and removably disposed within the packaging in a retained position. Further by way of clarity and explanation, the closure may be described herein as being in the form of a tamper evident cap (TEC). However, the tracking system and method of implementation of the present invention may be utilized with other closures, different from the type or category specifically set forth herein.

In accordance with the present invention, the closure, even while retained in the packaging, includes a label connected to an exterior surface thereof, and further, this label includes a "coded identifier" formed on a visually exposed surface thereof. In addition, when the closure and attached label are in the packaging, the label is arranged in a substantially compacted or reduced size, hereinafter referred to as a "reduced orientation". Such a reduced orientation can include the label being folded, rolled or otherwise disposed into a position which reduces its overall size and configuration. As a result, the substantially reduced orientation of the label facilitates its packaging along with the closure, while being attached thereto.

As explained in greater detail hereinafter, upon an opening of the packaging, typically for attaching the closure to a container, an at least partial exposure of the closure to an exterior of the packaging occurs. Moreover, at least a portion of the container may be disposed within the packaging to accomplish an "attached relation" between the closure and the container. Again, for purposes of clarity and explanation, the referred to container may be in the form of a syringe, including a pre-filled syringe, of the type used in many medical facilities. In addition, the container, being in the form of a syringe, is cooperatively structured with the closure, which as noted previously herein, may be in the form of a tamper evident cap (TEC) to facilitate an original securement and/or secure, tamper evident attachment therebetween. However, as with the aforementioned closure, the tracking system and method of implementation may be operatively associated with other type containers including, but not limited to, other type medical containers.

In most cases, if not all, once the closure and the container are in attached relation to one another, they will be concurrently removed from the packaging, preferably by exerting an outwardly directed force on the container. The disposition, configuration and overall structuring of the label results in it being disposed or selectively positioned from the reduced orientation to an expanded orientation either upon or subsequent to the removal of the attached closure and container from the packaging. Once in the expanded orientation, the dimension and configuration of the label facilitates it being connected to the container concurrently to it being connected or attached to the closure. Therefore, in at least one embodiment the label is disposed and structured to be concurrently attached to the exterior of both the closure and the container and is more precisely disposed in interconnecting relation therebetween.

Also in accordance with the present invention and as set forth above, the label preferably includes a "coded identifier" disposed or formed on the exposed surface thereof. In addition, the coded identifier includes at least a first coded segment and a second coded segment, each disposed on the label in aligned relation with a different one of the closure and the container, when the label is attached thereto in the expanded orientation. In more specific terms, when the label is concurrently attached to the exterior of the closure and the container, each of the first and second coded segments is attached in aligned relation with a different one of the closure and container. Such an aligned relation, in combination with the different first and second coded segments, serves to establish and/or define a "matching relation" and/or matching identity of the closure and container, as originally attached, when the label is connected to both the closure and the container, in the expanded orientation.

Additional structural and operative features of the system, which facilitate its method of implementation, include the coded identifier, as well as each of the first and second coded segments, being machine-readable. As used herein, the term "machine-readable" is intended to be interpreted in its broadest sense. As such, the machine-readable characteristics of the at least first and second coded segments may include, but not be limited to, indicia to allow for being scanned and read with known bar-code, infra-red (RFID) technology, or optically scanned using other technology, or photographed, or otherwise electronically/digitally read, as may be already known or yet to become available. The indicia of the coded identifier can include, but is not limited to, the first and second indicia segments having other forms, whether alpha-numeric indicia, or a variety of other forms. Accordingly, the format of the at least first and second coded segments may be both visually observable and machine-readable as set forth above. Further, the first and second coded segments may comprise a substantially common coded indicia, or in the alternative, may have at least partially different coded indicia. In the latter operative situation, the different coded indicia on the at least first and second coded segments are cooperatively structured to define the aforementioned matching relation and/or identifying relation of the closure and the container as components that were originally and initially combined.

Yet additional operative features which facilitate utilization of the tracking system of the present invention, as well as its method of implementation, include structural features associated with the aforementioned packaging. As such, the packaging may be generally described as an "ergonomic butterfly" assembly, which is operative, at least when facilitating the attachment of the container to the closure, to maintain an at least partial sterile environment, at least with regard to the connector that is to be associated with the container, such as a pre-filled syringe.

More specifically, the packaging includes a base having a hollow interior sufficiently dimensioned and configured to retain the closure therein. In addition, the base has a supportive, stabilizing platform secured to an upper or outer end thereof. The base and stabilizing platform include an access opening disposed in communicating relation with the hollow interior of the base, as well as a connecting portion of the closure. A cover is disposed in enclosing, overlying and substantially sealing relation to the access opening and is removably disposed to an exterior portion of the stabilizing platform. The cover and the platform may be cooperatively structured to facilitate a "peeling-back" of the cover, thereby opening the access opening and exposing at least the connecting portion of the closure. Moreover, the access opening is dimensioned disposed and configured to facilitate receipt and/or passage of at least a connecting portion of the container there-through so as to facilitate establishment of the original aforementioned "attached relation" between the closure and the container.

Once the packaging is opened, the container and the closure, while in the attached relation to one another, may be concurrently removed through the access opening. Such removal will result in an exposure of the label, as originally disposed in the reduced orientation. However, once on the exterior of the packaging, the label is disposable into an "expanded orientation" for attachment to the container, while the container is in the attached relation to the closure. Attachment to the exterior of the closure, as well as to the exterior of the container, may be accomplished through the provision of an "adhering surface" which may be defined by an undersurface of the label. The adhering surface may include any appropriate type of adhering material or structure such as, but not limited to, a glue, tape or other adhesive.

Therefore, it is emphasized that the first and second coded segments, which at least partially define the "coded identifier," are structured to establish an identifying, matching relation between the closure and the container, as being initially and originally connected into the attached relation to one another, thereby defining a unique combination of connected medical devices.

The tracking system and method of implementation according to the present invention provides for the detecting, inspecting, reading, recording, etc. of the coded identifier, including the at least first and second coded segments, of an originally combined and attached closure and container. Moreover, the inspection of the originally attached container and closure may occur at various points along a "distribution route". The distribution route, as used and described herein, is intended to include the various points, stations or locations including, but not limited to, a point of manufacture and/or assembly to a point of intended, authorized use. The distribution route may also include the registering, reading, detecting, recording etc. of the coded identifier, including at least the first and second coded segments, at one or more intermediate distribution and/or storage stations, locations, etc. between the point of manufacture and/or assembly and the intended point of use, such as where it is administered to a patient.

Therefore, at any point along the above noted distribution route an attempted or accomplished tampering of the closure or container may result in a separation therebetween. In the alternative, and in order to avoid detection of an unauthorized access, the original closure may be removed and abandoned. Thereafter, a different closure, possibly including a new or different coded segment and label, may be substituted therefor. Upon such an occurrence, the reading or scanning of the first and second coded segments would provide an indication that the inspected coded segments do not "match". In turn, this would provide a clear indication that the substituted closure was not the original closure attached to the syringe or other container.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
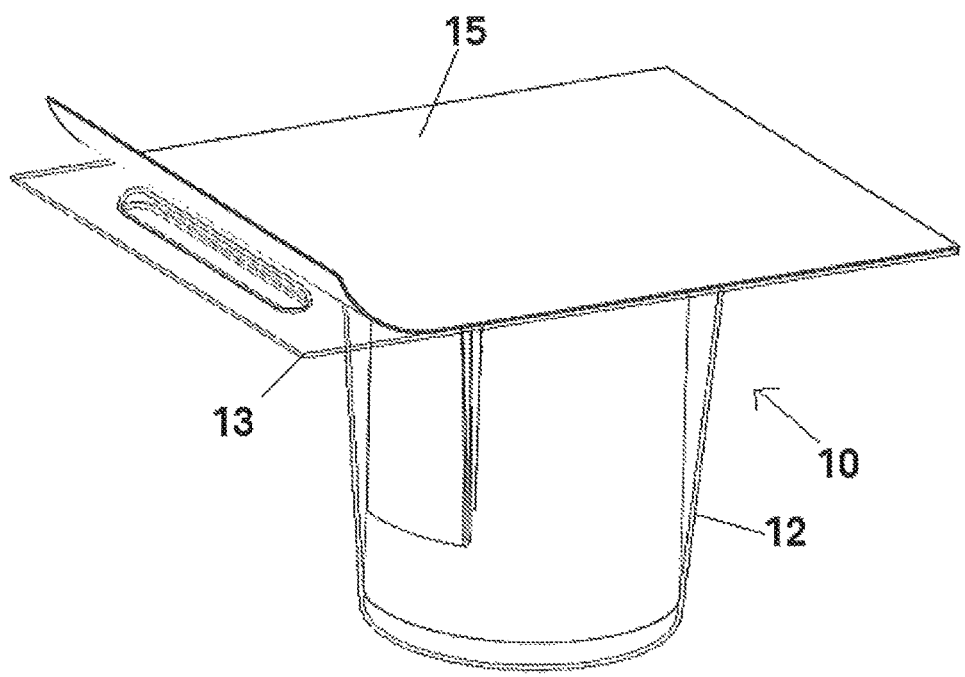
FIG. 1 is a perspective view of packaging for a closure that is sealed and removably retained therein along with a label attached thereto in a reduced orientation.

As set forth in the accompanying Figures, the present invention is directed to a tracking system and method of implementation which is operative with a packaging, as best illustrated in FIGS. 1 and 2-A and generally indicated as 10. The packaging 10 includes a base 12 having a hollow interior dimensioned and configured to removably retain a closure 14. As described and represented, the closure 14 may be in the form of a tamper evident cap (TEC) of the type intended for attachment to a container 16, which may be in the form of a syringe and/or a pre-filled syringe having a drug therein. However, the system and method of the present invention may be utilized with closures and containers other than a TEC 14 and/or syringe or pre-filled syringe 16.

In addition, the packaging 10 may be generally defined and described as an "ergonomic butterfly" packaging. As such, the packaging 10 includes a platform 13 which may be at least partially rigid or semi-rigid to facilitate gripping, handling and overall stability of the packaging 10. The packaging 10 may also include an outer cover 15 disposed in covering, at least partially sealing engagement relative to an access opening 17 extending through the platform 13 into communicating relation with the hollow interior of the base 12, as clearly represented in FIG. 2A.

Figure 2A:
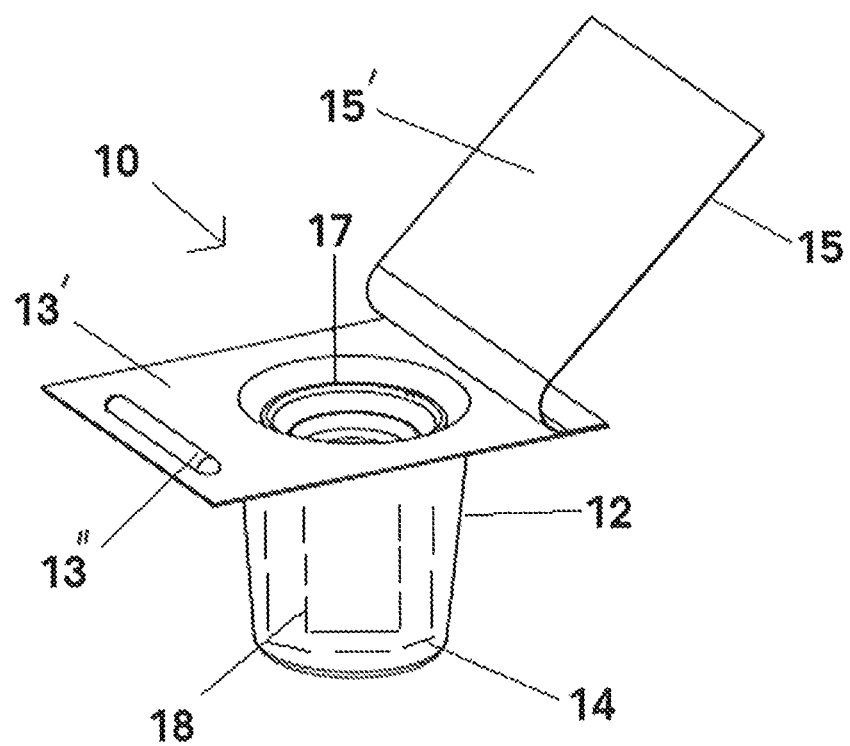
FIG. 2A is a perspective view with the packaging of the embodiment of FIG. 1 being opened to provide access to and partial exposure of the closure contained therein.
Figure 2B:
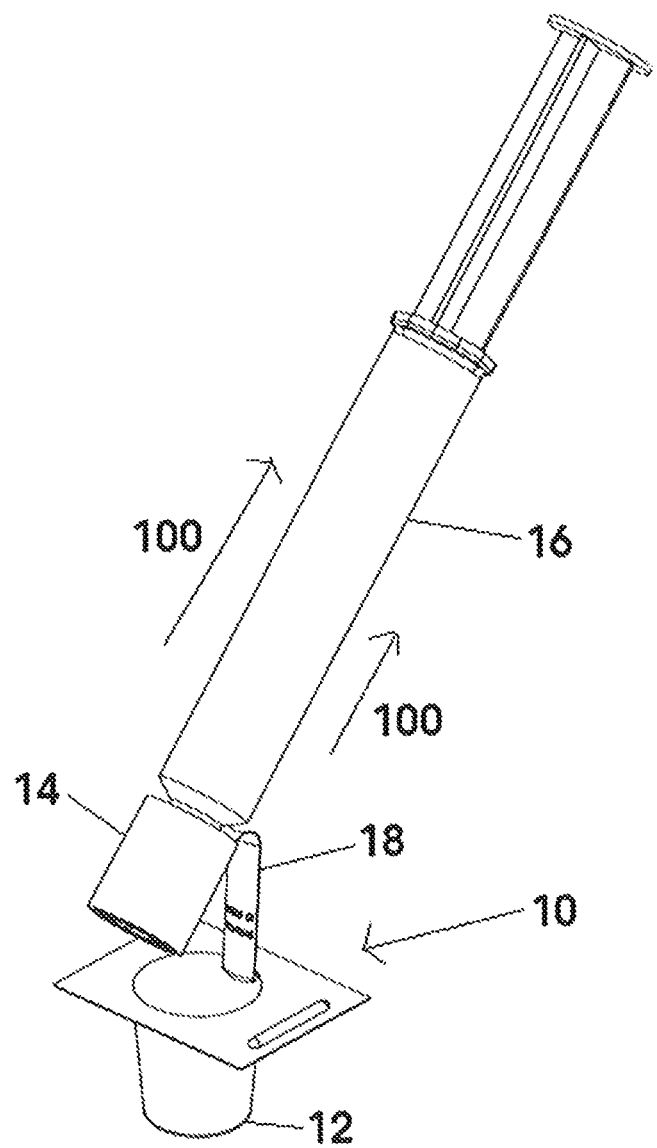
FIG. 2B is a perspective view in partial cutaway of a container, in the form of a syringe, at least partially entering the packaging to establish an attached relation between the container and the closure, wherein the attached closure and container are concurrently removed from the packaging.
Figure 2C:
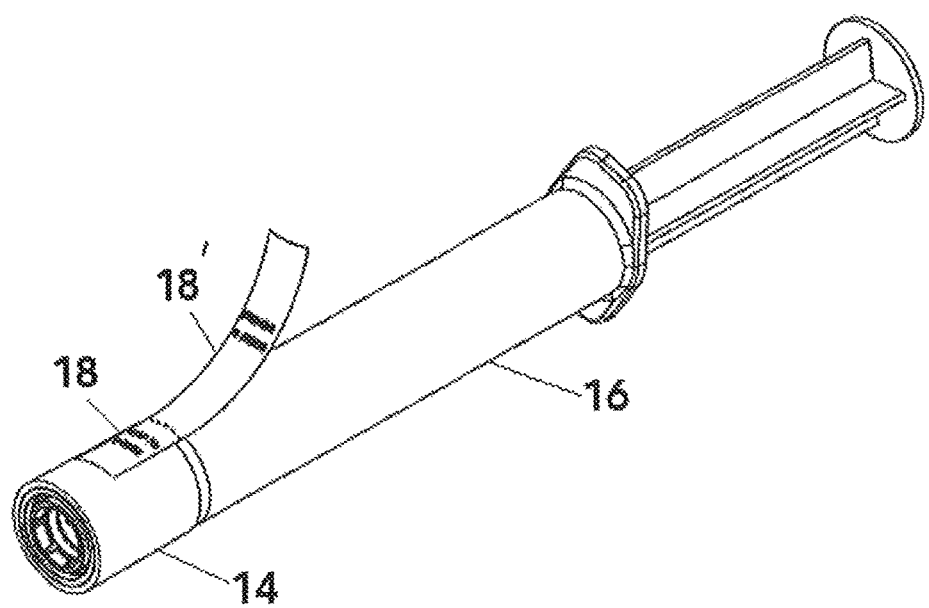
FIG. 2C is a perspective view in partial cutaway of the closure and container as originally attached wherein a label is disposed in an at least partially expanded orientation.
Figure 2D:
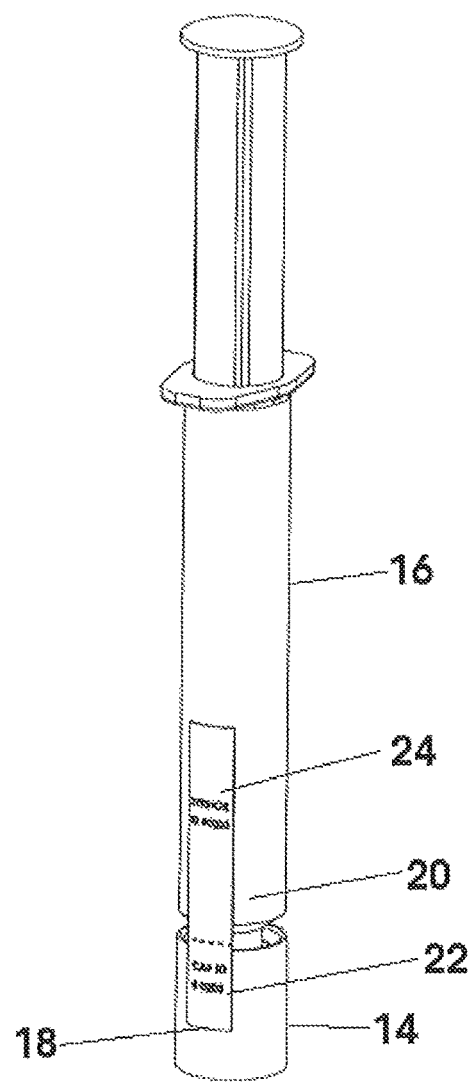
FIG. 2D is a perspective view in partial cutaway with the label disposed in an operative position connected concurrently to both the closure and the container, wherein a coded identifier is disposed in aligned, identifying relation with both the closure and the container.

As also represented in FIGS. 2B-2D, a label 18 is disposed within the interior of the base 12, concurrently to it being attached to the exterior surface of the closure 14. In order to facilitate the containment of both the closure 14 and the label 18 attached thereto, the label 18 is positioned into a reduced size orientation, hereinafter referred to as "reduced orientation". In use, the tracking system and method of implementation further include an opening of the packaging 10 by removal or "peeling-back" the cover 15 from the outer surface 13' of the platform 13. Moreover, when in its closed position as represented in FIG. 1, the cover 15 may overlie, cover and effectively seal the access opening 17. Securement of the cover 15 to the corresponding surface 13' in its overlying, sealing relation to the access opening 17 may be accomplished through the provision of an adhesive or other appropriate connector or attachment section 13". Yet additional facilities for initially and removably maintaining the cover 15 in the closed position of FIG. 1 may include an adhesive material disposed on either or both of the undersurface 15' of the cover 15 or the corresponding mating surface 13' of the platform 13. Such adhesive or other appropriate connecting material/structure should facilitate a sealing engagement of the cover in its closed orientation over the access opening 17, while still allowing an effective and efficient removal thereof into the open orientation of FIG. 2A. Such opening may preferably occur by allowing for the "peeling-back" of the cover 15, as set forth above.

Once the cover 15 is removed from its overlying, sealing relation to the access opening 17, the container and/or syringe 16 can be at least partially passed through the access opening 17 into direct, engagement with exposed portions of the closure 14. Such exposure thereby accommodates a threading or other connection between the container 16 and the closure 14, while the closure 14 is still within the interior of the base 12 of the packaging 10. Manipulation of the container 16 relative to the closure 14 provides the aforementioned "attached relation" therebetween. As a result, a unique combination of an originally attached closure 14 and container 16 is established. Once in the attached relation to one another, the closure 14 and the cover 16 are concurrently removed from the packaging 10 through the access opening 17, as schematically represented by directional arrows 100. Such removal may be accomplished by exerting a pulling or other appropriately directed force on the container 16, causing both the inserted portion of the container 16 and the closure 14 to be concurrently removed from the interior of the base 12 of the packaging 10.

It should be further noted that due to the connection of the label 18 to the exterior of the closure 14, the label 18 will also be removed from the interior of the base 12, along with removal of the closure 14. Therefore, as represented in FIGS. 2C and 2D, once the attached closure 14 and container 16 are disposed exteriorly of the packaging 10, the label 18 may assume or be disposed in an "expanded orientation." The expanded orientation is further defined by a substantially elongated configuration and an appropriately corresponding size of the label 18 allows for it to extend into an intended expanded operative position, as represented in FIG. 2D. Therefore, when in the intended expanded operative position, the label 18 is attached concurrently to both the exterior surfaces or portions of the closure 14 and the container 16. Such a simultaneous attachment of the label 18 in its expanded operative position to both the closure 14 and container 16 may be accomplished by the provision of an adhering undersurface 18' having one or more types of adhering material such as, but not limited to, glue, tape, various adhesive(s).

Figure 3:
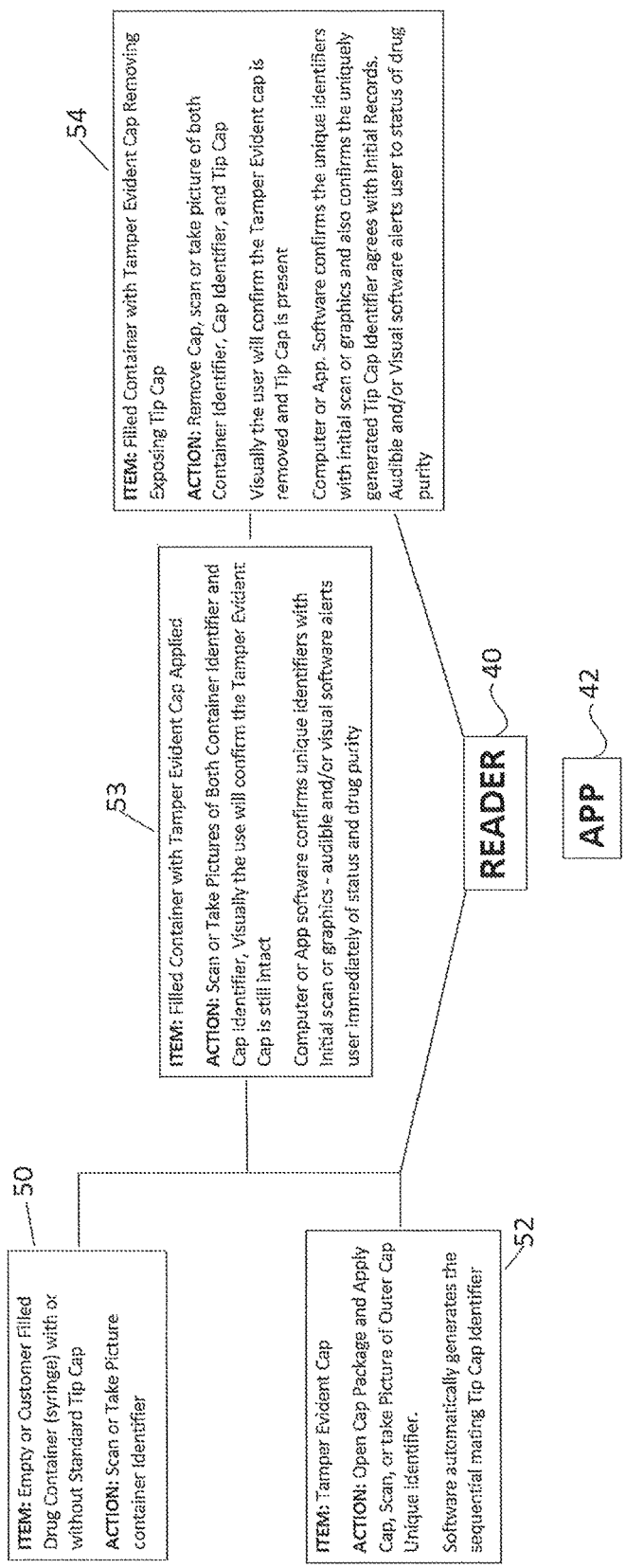
FIG. 3 is a schematic representation in block diagram form descriptive of a method of implementing the tracking system of the present invention.

With reference now to FIG. 2-D, another structural and operative feature of the tracking system and method of implementation includes the provision of a coded identifier, generally indicated as 20, formed on the outer, exposed surface of the label 18. As such, the coded identifier 20 includes at least a first coded segment 22 and a second coded segment 24. Each of the coded segments 22 and 24 may comprise various coded formats such as, but not limited to, alpha/numeric indicia, barcode and/or RFID tags/devices, optical scanning indicia and the like. In each such instance, the coded identifier 20, specifically including the first and second coded segments 22 and 24 may be "machine-readable", and capable of being scanned, electronically or digitally detected, photographed or otherwise "read" by an appropriate reader or scanning device 40 as schematically represented in FIG. 3.

In addition, the first and second coded segments 22 and 24 defining the coded identifier 20 may comprise a substantially common coded indicia, which establishes the original identity and "matching relation" between the closure 14 and the container 16. In contrast, the coded indicia which may define at least a portion of each of the first and second coded segments 22 and 24 may differ from one another, but be operatively and electronically "related" so as to indicate and define the aforementioned original identity and "matching relation" between the closure 14 and the container 16.

With reference again to FIGS. 2C and 2D, once the label 18 is disposed in its expanded orientation, it may be disposed in concurrently connected engagement with the exterior of the closure 14, as well as the exterior of container 16 as set forth above. However, such concurrent connection is further defined by each of the first and second indicia segments 22 and 24 being disposed in aligned and identifying relation with a different one of the closure 14 and container 16. In the represented embodiment of FIG. 2D, the first coded segment 22 is disposed in aligned, identifying relation with the closure 14, while the second indicia segment 24 is disposed in aligned, identifying relation with the container 16. Naturally, such order or represented alignment may be reversed.

As set forth above, one example of the tampering system and method of implementation of the present invention includes the closure 14 being in the form of a TEC, while the container is in the form of a pre-filled syringe 16. As such, the closure 14 may have tamper evident capabilities or structuring such as a multi-component configuration. As a result, a forced separation of one possible component of a TEC, namely, an outer sleeve or end cap 14' of the TEC/closure 14, will result in a separation thereof from the container 16, concurrently to an interior tip cap (not shown) remaining on the connecting or outer discharge port portion of the syringe 16. Such separation will further provide a visual indication that access to the syringe container 16 or its contents and/or a tampering thereof has been attempted.

With primary reference now to FIG. 3, a method of implementation of the tracking system of the present invention may include one or more of the procedures schematically represented. Moreover, the scanning, reading, detecting, etc. of the coded identifier 20, specifically including the first and second coded segments 22 and 24, is accomplished by the reader 40 having appropriate reading, scanning and/or detecting capabilities. In addition, a software application 42 is operatively connected or configured to provide and process the scanning, reading, recording, etc. procedures as well as to record, store, track, etc. the coded identifier 20 and more specifically, the matching or nonmatching coded indicia which at least partially defines the first and second coded segments 22 and 24. It is of further note that the software application 42 may be directly associated and/or operatively integrated into a machine and computing device having a processor, and ability to communicate with other servers/hardware, etc. to accomplish the intended recording, memorizing, comparing, storing, searching etc. procedures needed to establish the existence or nonexistence of the unique combination of closure 14 and container 16, as originally connected into the aforementioned "attached relation" as described with primary reference to FIGS. 2B-2D.

Still referring to FIG. 3, and as schematically represented at 50 and 52, the container or syringe 16 may be provided in a filled or unfilled state and may be scanned by reader 40 in such state. However, in at least one preferred embodiment as represented in FIGS. 2B-2D, the container 16 of may be in the form of the prefilled syringe disposed in the attached relation to the cover 14. The reader 40 may then scan the unique combination of the originally attached cover 14 and container 16, as at 50, 52. Once the label 18 is disposed in its expanded orientation and operative position, so as to expose the coded identifier 20, the attached and uniquely combined closure 14 and container 16 may be detected along the intended distribution route as at 50, 52, 53, 54, etc. as indicated, the distribution route, partially indicated as 53, may include a plurality of intermediate distribution and storage stations, prior to reaching its point or location of intended use as at 54. The reader 40 will scan the unique combination of attached closure 14 and container 16 at each point along the distribution route 53 and the maintenance of such original attachment between the closure 14 and the container 16 will be verified through the processing capabilities and features of the software application 42, as implemented by the reader/scanner 40.

Finally, at its point of intended use, such as where the contents of the syringe or container 16 is administered to a patient, the unique combination of the originally attached closure and container 16 is again electronically/digitally scanned, read, etc. to assure that the coded indicia, which at least partially defines the first and second coded segments 22 and 24 is as originally recorded and identifies the intended, original matching relation between the closure 14 and the container 16. Once verification of the original attached relation between the closure 14 and the container 16 has occurred, the contents of the container 16 may be safely administered or otherwise utilized in the intended manner.

As schematically represented in FIG. 3, a single reader 40 and attendant software application 42 is presented. However it should be apparent that due to the scanning, reading, inspecting of one or more of the attached closure 14 and container 16 combinations may be repeated at different ones of the points of distribution along the distribution route 50-54. Accordingly, a number of such readers 40 and operatively integrated software applications 42 may be utilized.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A tracking system for medical devices comprising:
    a closure and packaging for said closure,
    said closure initially and removably disposed within said packaging in a contained position,
    a label connected to said closure and disposed within said packaging in a reduced orientation with said closure,
    a coded identifier formed on an exposed surface of said label in a substantially reduced orientation; said coded identifier comprising at least a first and second coded segments,
    a container attached to said closure upon an opening of said packaging,
    said label disposed into an expanded orientation upon removal of said closure and said label from said packaging,
    said label disposed into interconnecting attached engagement with both said closure and said container when in said expanded orientation,
    each of said first and second coded segments disposed on said label in aligned relation with a different one of said closure and said container.

2. The tracking system as recited in claim 1 wherein said coded identifier is machine-readable.

3. The tracking system as recited in claim 2 wherein said first and second coded segments comprise a substantially common coded indicia, said common coded indicia cooperatively structured to define an original attached combination of said closure and said container.

4. The tracking system as recited in claim 2 wherein said first and second coded segments comprise different coded indicia; said different coded indicia cooperatively structured to define an original attached combination of said closure and said container.

5. The tracking system as recited in claim 1 wherein said label includes an adhering undersurface concurrently secured to said closure and said container, when said label is in said expanded orientation and said closure and said container are removed from said packaging.

6. The tracking system as recited in claim 1 wherein said closure comprises a tamper evident cap structured for at least partially removable attachment to said container; said removable attachment visually indicative of attempted access to contents of said container.

7. The tracking system as recited in claim 6 wherein said container comprises a syringe.

8. The tracking system as recited in claim 1 wherein said packaging comprises a base including a hollow interior dimensioned and configured to removably retain said closure therein; said base including an access opening disposed in communicating relation with said at least one closure; said access opening dimensioned and configured to receive a portion of said container there through in attached relation to said closure.

9. The tracking system as recited in claim 8 wherein said packaging further comprises a cover disposed in removable covering and initially sealing relation to said access opening.

10. The tracking system as recited in claim 9 wherein said base and said access opening are configured for concurrent removal of said closure and said container from said packaging, when said closure and said container are in said attached relation.

11. The tracking system as recited in claim 10 wherein said label is initially disposed in said reduced orientation upon said removal of said closure and said container from said packaging, when said closure and said container are in said attached relation.

12. The tracking system as recited in claim 11 wherein said label is disposed in said expanded orientation and in attached interconnecting engagement with both said closure and said container, subsequent to removal of said closure and said container from said packaging.

13. The tracking system as recited in claim 8 wherein said packaging further comprises a platform; said platform extending outwardly from said access opening and including an aperture disposed in aligned relation with said access opening; said cover removably attached to said platform in covering relation to said aperture and said access opening.

14. A method of implementing a tracking system for medical devices, said method comprising:
    structuring a label to include a coded identifier on an exposed surface thereof and attaching the label to a closure,
    disposing the closure and the label in a packaging, while the label is in a reduced orientation,
    positioning a container at least partially within said packaging in attached relation to said closure,
    removing the attached closure and container from the packaging concurrent to said label being in said reduced orientation,
    configuring the coded identifier to include at least first and second coded segments,
    disposing the label into an expanded orientation upon removal of the attached closure and container from the packaging,
    attaching the label, while in the expanded orientation, to the container and in interconnecting relation between the closure and the container, and aligning each of said first and second coded segments with a different one of the cover and the container.

15. The method as recited in claim 14 comprising cooperatively configuring the first and second coded segments to include a substantially common coded indicia, configuring the substantially common coded indicia to define an original attached combination of the closure and the container.

16. The method as recited in claim 14 comprising cooperatively configuring the first and second segments to include at least partially different coded indicia; configuring the at least partially different coded indicia to define an original attached combination of the closure and the container.

17. The method as recited in claim 14 comprising structuring the closure to define a tamper evident cap structured for removable attachment to the container; further structuring the tamper evident cap to provide a visual indication of attempted access to the container, upon an at least partial removal of the tamper evident cap from the container.

18. The method as recited in claim 17 comprising structuring of the container to define a syringe.

19. The method as recited in claim 14 comprising structuring the coded identifier and the first and second coded segments to be machine-readable.

\* \* \* \* \*